(12) United States Patent
Krishnamurthy

(10) Patent No.: US 8,945,283 B1
(45) Date of Patent: Feb. 3, 2015

(54) APPARATUSES AND METHODS FOR GAS-SOLID SEPARATIONS USING CYCLONES

(71) Applicant: UOP LLC, Des Plaines, IL (US)

(72) Inventor: Sujay R. Krishnamurthy, Hoffman Estates, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 14/228,671

(22) Filed: Mar. 28, 2014

(51) Int. Cl.
*B01D 45/12* (2006.01)
*B04C 3/04* (2006.01)
*B04C 3/00* (2006.01)

(52) U.S. Cl.
CPC ............. *B04C 3/04* (2013.01); *B04C 2003/006* (2013.01)
USPC .................. 95/269; 55/347; 55/348; 55/416; 55/418; 55/447; 55/449; 55/456; 55/457; 95/271

(58) Field of Classification Search
USPC ........... 55/347, 348, 416, 418, 447–449, 456, 55/457, 394, 396; 95/271
See application file for complete search history.

(56) References Cited

U.S. PATENT DOCUMENTS

| | | | |
|---|---|---|---|
| 4,537,608 A * | 8/1985 | Koslow | 55/337 |
| 5,372,707 A | 12/1994 | Buchanan et al. | |
| 5,643,537 A | 7/1997 | Raterman et al. | |
| 5,648,544 A | 7/1997 | Semeria et al. | |
| 5,681,450 A | 10/1997 | Chitnis et al. | |
| 5,690,709 A | 11/1997 | Barnes | |
| 5,779,746 A | 7/1998 | Buchanan et al. | |
| 5,914,433 A | 6/1999 | Marker | |
| 6,166,282 A | 12/2000 | Miller | |
| 6,902,593 B2 | 6/2005 | Miller et al. | |
| 7,648,544 B2 | 1/2010 | Dewitz et al. | |
| 7,985,282 B2 | 7/2011 | Castagnos, Jr. et al. | |
| 8,025,717 B2 | 9/2011 | Dries et al. | |
| 8,419,835 B2 | 4/2013 | Krishnamurthy et al. | |
| 2013/0152525 A1 | 6/2013 | Brandner et al. | |

FOREIGN PATENT DOCUMENTS

| | | |
|---|---|---|
| AU | 2009100485 | 7/2009 |
| EP | 298671 | 1/1989 |
| IN | 200804759 | 8/2008 |

(Continued)

OTHER PUBLICATIONS

Peng et al., "Experimental study of the vortex end in centrifugal separators . . . ," Chemical Engineering Science (2005), 60(24), 6919-6928.

(Continued)

*Primary Examiner* — Dung H Bui

(57) ABSTRACT

Cyclones for gas-solid separators are provided, which are especially applicable for use in a downflowing third stage separator (TSS) for the removal of dust particles, such as solid catalyst fines, from the flue gas streams exiting the catalyst regenerator in fluid catalytic cracking (FCC) processes. A cyclone comprises a barrel and a central hub disposed within the barrel to provide an annular section between the outer diameter of the central hub and the inner diameter of the barrel. Swirl vanes extend radially into the annular section. A shield is disposed at least partially within the annular section and at least partially within the swirl vanes. The shield radially divides the annular section into an inner annular portion and an outer annular portion.

20 Claims, 2 Drawing Sheets

(56) References Cited

FOREIGN PATENT DOCUMENTS

| | | |
|---|---|---|
| IN | 255593 | 3/2013 |
| WO | WO 2007/081832 | 7/2007 |

OTHER PUBLICATIONS

Hoffmann et al., "Effect of pressure recovery vanes on the performance of a swirl tube . . . ," Energy & Fuels (2006), 20(4), 1691-1697.

* cited by examiner

APPARATUSES AND METHODS FOR GAS-SOLID SEPARATIONS USING CYCLONES

BACKGROUND OF THE INVENTION

Embodiments of the invention relate to apparatuses and methods for gas-solid separation and particularly for the separation of gas effluents from fluidized particle beds, including those used for catalytic reactions and catalyst regenerations involving solid catalysts. Example embodiments relate more particularly to cyclone separators used in gas-solid separators.

Fluidized beds are currently used extensively in major industries including oil refining, petrochemical production, coal and mineral beneficiation, metallurgical applications, food processing, etc. Fluidized beds of solid particles, and particularly those operating in the bubbling regime, advantageously provide very uniform gas-solid contacting conditions due to thorough mixing. Fluidization generally causes not only local mixing but also large-scale circulation within the bed. These benefits of solid particle fluidization, however, are not without consequences. The most significant of these is the entrainment (elutriation or carryover) of solid particles due to the passage of gas bubbles through the dense phase of the fluidized solid particle bed and breakage of these bubbles at the surface of the dense phase. The bursting action of the bubbles throws large amounts of the particulate solids into the dilute phase directly above the dense phase. This in turn causes entrainment of particles having a sufficiently small diameter, namely such that their terminal velocity (which decreases with decreasing particle size) is below the superficial velocity of the rising gas.

Particular fluidized bed systems of practical interest in the refining and petrochemical fields include those used in catalytic conversions in the presence of a solid particulate catalyst. The use of fluidized beds of catalyst is favorable, for example, in conversion processes in which catalyst deactivation, due to the accumulation of carbonaceous deposits (coke) during the course of the conversion, occurs rapidly. In such cases, deactivated catalyst from a reaction zone must be passed to a regeneration zone for removal of the accumulated deposits by combustion, followed by return of the regeneration catalyst back to the reaction zone. Fluidized beds of catalyst in both the catalytic reactor and catalytic regenerator allow for continuous circulation of spent (coked) and regenerated catalyst between these apparatuses.

One example of a refining process utilizing fluidized bed reaction and regeneration zones is fluid catalytic cracking (FCC). FCC is applicable for the conversion of relatively high boiling or heavy hydrocarbon fractions, such as crude oil atmospheric and vacuum column residues and gas oils, to produce more valuable, lighter hydrocarbons and particularly those in the gasoline boiling range. The high boiling feedstock is contacted in one or more reaction zones with a particulate cracking catalyst that is maintained in a fluidized state, under conditions suitable for carrying out the desired cracking reactions. In the fluidized contacting or reaction zone, carbonaceous and other fouling materials are deposited on the solid catalyst as coke, which reduces catalyst activity. The catalyst is therefore normally conveyed continuously to another section, namely a regeneration zone, where the coke is removed by combustion with an oxygen-containing regeneration gas. The resulting regenerated catalyst is, in turn, continuously withdrawn and reintroduced in whole or in part to the reaction zone.

More recently, fluidized bed systems have been applied in the production of light olefins, particularly ethylene and propylene, which are valuable precursors for polymer production. The light olefins are desirably obtained from non-petroleum feeds comprising oxygenates such as alcohols and, more particularly, methanol, ethanol, and higher alcohols or their derivatives. Methanol, in particular, is useful in a methanol-to-olefin (MTO) conversion process described, for example, in U.S. Pat. No. 5,914,433. These patents and others teach the use of a fluidized bed reactor with continuous circulation of spent catalyst from the reactor to a regenerator. The regenerator can similarly contain a fluidized bed of solid catalyst particles for carrying out regeneration by the combustion of deposited coke.

In processes such as FCC and MTO, the use of fluidized particle beds in the reaction and regeneration zones leads to entrainment of solids into the gaseous effluents from these zones. In the case of the reaction zone, catalyst particles can exit with the reactor effluent, containing the desired reaction products (e.g., gasoline boiling range hydrocarbons in the case of FCC or light olefins in the case of MTO). Likewise, catalyst particles may similarly become entrained in the combustion gases exiting the catalyst regenerator (e.g., containing nitrogen, $CO_2$, CO, and $H_2O$). Catalyst fines contained in the regenerator flue gas effluent are known to interfere with downstream power generation equipment such as the expander. In general, the losses of entrained catalyst from a fluidized bed, such as a catalytic reactor or catalyst regenerator, result in increased costs, particularly on an industrial scale. This is especially true considering the high cost of the zeolite-containing catalysts used currently in FCC and the non-zeolitic molecular sieve catalysts (e.g., silicoaluminophosphates or SAPOs) used currently in MTO.

To minimize losses of entrained catalyst particles, a number of gas-solid separators have been proposed for use in disengagement or separation zones, located above the dense bed phase, in reactors and regenerators having fluidized solid catalyst beds. These separators, including cyclones, filters, screens, impingement devices, plates, cones, and other equipment, have been used with varying success. Cyclone separators have gained widespread use in both FCC and MTO, as described, for example, in U.S. Pat. No. 8,419,835 and in U.S. Pat. No. 6,166,282. Cyclone separators have been applied in both the catalytic reactors and catalyst regenerators of these conversion processes.

Refiners have also used a cyclone-containing third stage separator (TSS), external to the catalyst regenerator, to remove catalyst fines from the FCC regenerator flue gas (i.e., the combustion gas exiting the regenerator). These devices have typically been used in power recovery installations to protect expander blades. In the TSS, flue gas from the FCC catalyst regenerator is passed through a number of high efficiency cyclonic elements arranged in parallel and contained within the TSS vessel. The flue gas enters the vessel through a flow distributor that evenly distributes the gas to the individual cyclone elements. After catalyst particulates are separated from the flue gas in the cyclones, the clean flue gas leaves the separator. The solid particulates are concentrated in a small stream of gas, called the underflow gas, which exits the bottom of the TSS.

Cyclones and other separation devices exhibit equipment (e.g., metal) erosion due to the high velocity of gases used and the interaction between these gases, containing entrained solid particles, and the walls of these devices. Erosion leads to a reduction in equipment life and/or increased costs due to maintenance and downtime. For example, it has been observed that, over the course of continuous operation over a prolonged time period on the order of several years, considerable erosion may occur within the separator cyclone barrel. If sufficiently severe, such erosion may require localized repair or replacement of the entire cyclonic separator, which may necessitate shutdown of the TSS and possibly the FCC system as a whole.

Erosion issues mainly arise from a large central hub outside diameter within the barrel of the cyclone. Typically, swirling flow in an annular section between the barrel and the central hub contracts from a diameter corresponding to the central hub outside diameter to the center of a cyclone barrel, with an associated increase in the velocity and a low pressure region at the center. As a result, the gas stream at the barrel's inner diameter (i.e., the barrel wall) momentarily contracts to a smaller diameter. This causes an abrupt change in the particle flow direction and erodes the barrel wall.

Other devices are designed to circumvent the erosion problem by simply reducing the central hub diameter. However, for a given helical pitch (turns/angle), the path traced by the helical curve is more vertical at the hub and more horizontal at the cyclone's barrel. For this reason, the flow at the center will have a more vertical trajectory than at the outside, which is undesirable from a separation perspective. This disadvantage can be circumvented by varying the height of the swirl vane along the radius, such as by using a small height at the central hub and a larger height at the barrel. However, this creates a potential for structural vibration issues due to the large span.

There is therefore an ongoing need in the art for apparatuses and methods that promote the desired separation of solids (e.g., catalyst particles), from gases (e.g., reactor and regenerator effluents) into which these solid particles are entrained, while simultaneously mitigating erosion and consequent particle attrition.

SUMMARY OF THE INVENTION

One aspect of the invention involves a cyclone for a gas-solid separator. The cyclone comprises a barrel and a central hub disposed within the barrel to provide an annular section between the outer diameter of the central hub and the inner diameter of the barrel. Swirl vanes extend radially into the annular section. A shield is disposed at least partially within the annular section and at least partially below the swirl vanes. The shield radially divides the annular section into an inner annular portion and an outer annular portion.

Another aspect of the invention provides a gas-solid separator. A gas-solid separator comprises an upper tube sheet, a lower tube sheet, and at least one cyclone extending through the tube sheets. The cyclone comprises an impure gas inlet at an upper end of a barrel above the upper tube sheet, a solid particle outlet at a lower end of the barrel between the upper tube sheet and the lower tube sheet, and a purified gas outlet below the lower tube sheet. The cyclone further comprises a barrel, a central hub disposed within the barrel to provide an annular section between the central hub and the barrel, swirl vanes extending radially into the annular section, and a shield disposed at least partially within the annular section and at least partially below the swirl vanes. The shield radially divides the annular section into an inner annular portion and an outer annular portion. Processes for purifying a gas stream contaminated with solid particles are also provided.

DETAILED DESCRIPTION OF THE INVENTION

Figure 1:
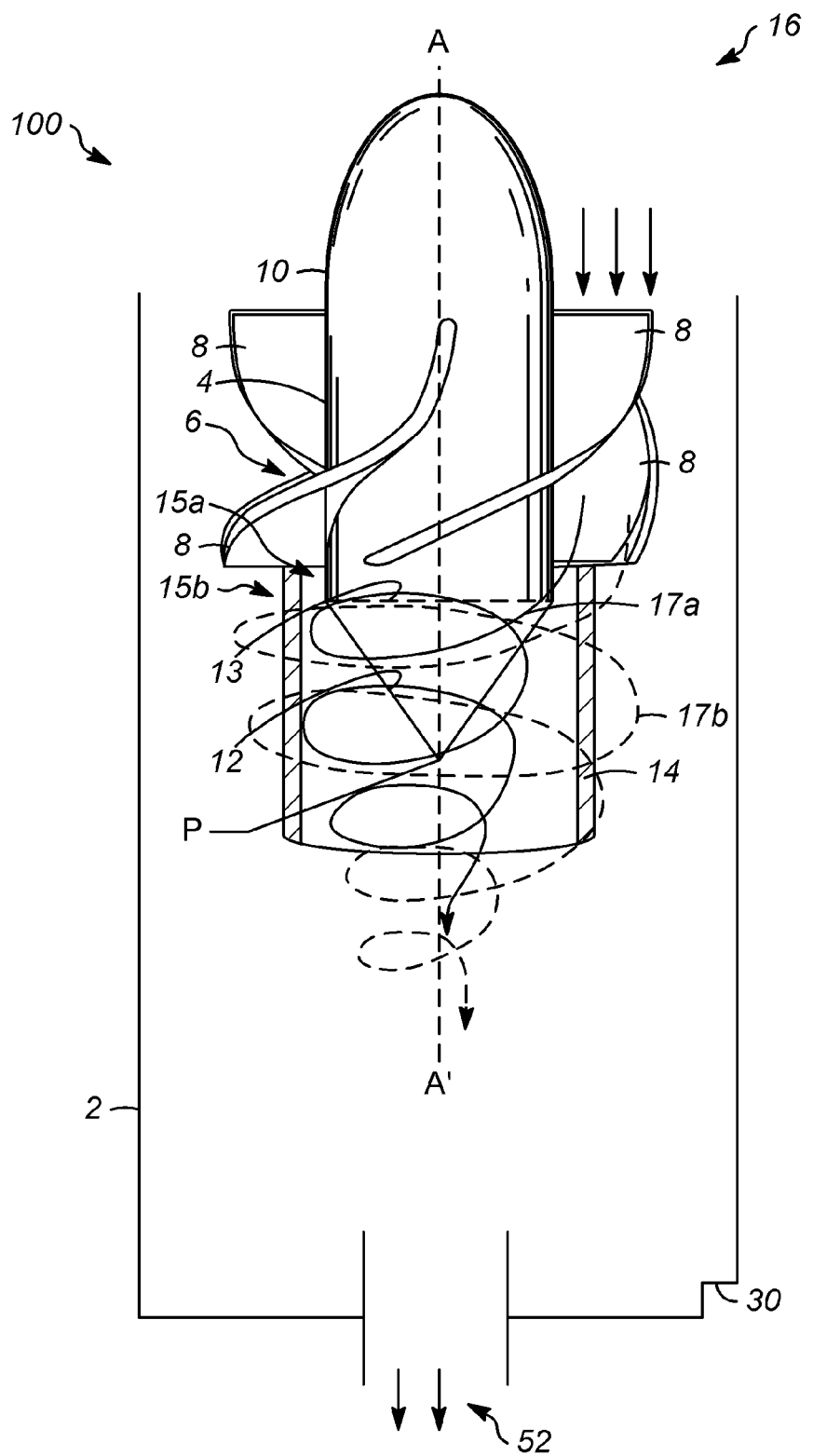
FIG. 1 is a partial cutaway view of a representative cyclone according to an embodiment of the invention.

Embodiments of the invention involve apparatuses and methods for the separation of solid particles from gas streams contaminated with such particles. Example embodiments particularly relate to such apparatuses and methods in which particle attrition and/or metal erosion are reduced, and/or separation efficiency increased, compared to conventional gas-solid separation methods.

Particular applications of apparatuses and methods are in cyclone separations of catalytic reactor or catalyst regenerator effluent gases containing solid catalyst particles, and especially those applications known to be presently carried out using an external third stage separator (TSS) to clean the particle-containing effluent gas (i.e., combustion product gas) from a fluid catalytic cracking (FCC) catalyst regenerator, often after undergoing initial stages of cyclone separation within the regenerator. Due to these initial stages (e.g., first and second stages) of separation, solids in the effluent of the FCC catalyst regenerator, which can serve as a feed gas stream in example apparatuses and methods, are typically in the form of fine dust. For example, the average size of solid particles, namely catalyst fines, in this gas stream is generally in the range from about 1 micron ($\mu m$) to about 75 $\mu m$, and often in the range from about 5 $\mu m$ to about 50 $\mu m$. The high gas velocities required to "de-dust" the FCC catalyst regenerator flue gas have given rise to concerns of equipment (metal) erosion, as discussed above.

Although particularly applicable for use in TSS apparatuses external to an FCC catalyst regenerator, the apparatuses and methods described herein are broadly applicable to gas-solid separators having one or a plurality of cyclones that may be used in any number of industrial applications, and especially in fluidized bed applications in which solid particles tend to become entrained in gases exiting the dense bed phase and are desirably removed. Examples include gas effluent streams from fluidized catalyst beds used in the catalyst reaction zone and/or catalyst regeneration zone of FCC or MTO processes. The cyclones may be used in a vessel external to a reactor or regenerator vessel that contains a disengagement or separation zone above a dense fluidized bed zone. Such external vessels, in contrast to the reactor or regenerator vessel, are normally configured for flow of the solid particle containing feed gas in the downward direction.

Example embodiments provide a cyclone for a gas-solid separator. The cyclone comprises a barrel, which may be hollow and generally cylindrical, and may extend axially within the separator. A central hub is disposed within the barrel, for example concentrically, to provide an axially extending annular section between the outer diameter of the central hub and the inner diameter of the barrel. Swirl vanes extend radially into the annular section. A shield is disposed at least partially within the annular section and at least partially below the swirl vanes. The shield radially divides the annular section into an inner annular portion and an outer annular portion.

The inner annular portion can be defined radially between an outer diameter of the central hub and the shield, and the outer annular portion can be defined radially between the shield and an inner diameter of the barrel. The inner annular portion can define a radial distance between about 10% and about 90% of an annulus of the annular section, and the outer annular portion can define a remainder of the annulus of the annular section (i.e., about 90% to about 10%).

In an example embodiment, a top of the shield is axially disposed above a contracting portion of the central hub, and a bottom of the shield is axially disposed below the contracting portion of the central hub, and preferably is disposed below the bottom of the central hub. A "contracting portion" of the central hub refers to a portion of the central hub at which a diameter of the central hub begins to decrease, i.e., a portion where the central hub begins to radially contract. In another example embodiment, a top of the shield is axially disposed above a bottom of the central hub, and a bottom of the shield is axially disposed below the bottom of the central hub. In some example embodiments, the shield is fixedly coupled to one or more bottom portions of the swirl vanes.

Other example embodiments provide a gas-solid separator, such as a third stage separator (TSS) comprising an upper tube sheet, a lower tube sheet, and at least one cyclone extending through the upper and lower tube sheets. The cyclone has an impure gas inlet at an upper end of a barrel, extending above the upper tube sheet; a solid particle outlet at a lower end of the barrel between the upper tube sheet and the lower tube sheet; and a purified gas outlet extending below the lower tube sheet. The cyclone comprises the features described above. Preferably, the gas-solid separator comprises a plurality of such cyclones (e.g., from about 5 to about 300 cyclones, depending on the particular application, though more or fewer cyclones can be provided).

Still other example embodiments provide a process for purifying a gas stream contaminated with solid particles. The process comprises feeding the gas stream to a process gas inlet of a gas-solid separator, wherein the gas-solid separator further comprises a plurality of cyclones, each cyclone comprising a barrel, an impure gas inlet at an upper end of the barrel, a solid particle outlet at a lower end of the barrel, a purified gas outlet, a central hub disposed within the barrel to provide an annular section disposed between the central hub and the barrel, swirl vanes extending radially into the annular section, and a shield disposed at least partially within the annular section and at least partially below the swirl vanes, wherein the shield radially divides the annular section into an inner annular portion and an outer annular portion. The process gas inlet is in communication with the impure gas inlets of the plurality of cyclones. The process further comprises withdrawing an underflow gas stream from a particle-rich gas outlet in communication with the solid particle outlets of the plurality of cyclones, and withdrawing a clean gas stream from a particle-lean gas outlet in communication with the purified gas outlets of the plurality of cyclones. A representative gas stream is an effluent from a catalytic reaction zone or a catalyst regeneration zone of an FCC process or an MTO process. In example embodiments, in each of the plurality of cyclones, the swirl vanes impart a helical or spiral motion to the gas stream. Also, in example embodiments, in each of the plurality of cyclones, the shield directs the gas stream into the inner and outer annular portions. The gas stream in the inner annular portion can provide an inner swirling flow, and the gas stream in the outer annular portion can provide an outer swirling flow.

Example embodiments provide, among other things, cyclones for gas-solid separators. Example cyclones are especially applicable for use in a downflowing (or so-called "uniflow") third stage separator (TSS) for the removal of dust particles, such as solid catalyst fines, from the flue gas streams exiting the catalyst regenerator in FCC processes. The cyclones, however, are also broadly applicable to the removal of solid particles from gas streams in any number of applications where such removal is desired, particularly with respect to gas effluent streams from fluidized catalyst processes such as catalytic reactions and catalyst regenerations. Example process streams include those encountered in FCC as well as MTO processes, as described above.

Turning now to the drawings, a cyclone 100 according to an example embodiment is depicted in FIG. 1. The cyclone 100 includes a hollow barrel 2 that is normally cylindrical in shape and extends axially. A central hub 4 is disposed within the barrel 2 in example embodiments (but not necessarily) in a concentric manner and extends axially such that axis A-A' of central hub 4 and the barrel 2 are aligned to provide a symmetrical flow geometry. The central hub 4 may have either a solid (i.e., not hollow) configuration or a hollow configuration. Other example barrels and central hubs are shown and described in commonly assigned U.S. Pat. No. 8,419,835 and in commonly assigned U.S. Pat. Pub. No. 2013/0152525.

Because both the central hub 4 and the barrel 2 extend axially, an axially extending annular section 6 is provided in the space between these elements of the cyclone 100. Particularly, the annular section 6 is disposed radially between the outer diameter of the central hub 4 and the inner diameter (wall) of the barrel 2. Swirl vanes 8, which may be helical, extend radially into a portion of the annular section 6. In the case of helical swirl vanes, it will be appreciated that a single vane may be used, extending circumferentially around the central hub 4 and also extending gradually in an axial direction (i.e., having an axial "pitch"), to thereby extend over the axial length of the swirl vane. Other example swirl vanes are shown and described in commonly assigned U.S. Pat. Pub. No. 2013/0152525, though still other configurations for the swirl vanes are possible. The barrel 2, the central hub 4, and the swirl vanes 8 may be fabricated as a unitary piece, or assembled from multiple components. In an example assembly method, the central hub 4 and the swirl vanes 8 are co-fabricated, and the assembled component is inserted into the barrel 2. Connecting members, e.g., notches and hubs, mating hooks, etc., may be provided on the swirl vanes 8, the central hub 4, and/or the wall of the barrel 2, as will be appreciated by those of ordinary skill in the art, to couple the central hub 4 and the swirl vanes to the barrel.

In the cyclone 100 shown in FIG. 1, the central hub 4 has both an upper, non-tapered section 10 and a lower, tapered section 12 (the lower, tapered section can be considered the section below line 13). The upper, non-tapered section 10 may be a cylindrical section, while the lower, tapered section 12 may be, for example, in the form of a conical end cap. A top of the central hub 4 may have a hemispherical configuration. The terms "upper" and "lower" are used herein to reference relative axial heights when the cyclone 100 is positioned for its normal downflow operation (i.e., with gas flowing from the "upper" part to the "lower" part of the cyclone). The terms are not meant to require that the cyclone 100 to be oriented in any particular position. In other example embodiments, the central hub 5 includes only a non-tapered (e.g., generally cylindrical) section, with the lower, tapered section 12 (i.e., the section below line 13) being omitted.

A generally cylindrical shield 14 is disposed within the cyclone 100, at least partially within the annular section 6 and at least partially below the swirl vanes 8. Particularly, a diameter of the shield 14 is radially disposed at least partially between an outer diameter of the central hub 4 (as shown in the cyclone 100, an outer diameter of the upper, non-tapered section 10) and an inner diameter (wall) of the barrel 2. The diameter of the shield 14 radially divides the annulus of the annular section 6 into concentric inner and outer annular portions 15a, 15b. This radial division, which can be defined by the diameter of the shield 14, can be substantially even (50%-50%, at the center point of the annulus) or uneven. For example, the inner annular portion 15a can define a radial distance that is anywhere from about 10% to about 90% of the annulus of the annular section 6, with the outer annular portion 15b defining a remainder of the annulus of the annular section (e.g., about 90% to about 10%).

The shield 14 is axially disposed so that the top of the shield is disposed above a contracting portion of the hub; that is, a portion of the central hub 4 at which the diameter of the central hub begins to decrease (in other words, begins to radially contract). In FIG. 1, this portion is at the bottom of the non-tapered section 10 at line 13, so that the top of the shield is disposed above line 13. If the central hub does not include the lower, tapered section 12, or otherwise does not decrease in diameter or contract at a lower section, the top of the shield can be disposed above the bottom of the central hub.

The top of the shield 14 preferably is disposed axially below the swirl vanes 8. However, a portion of the shield may be partially disposed over a portion of the swirl vanes, so long as the shield is disposed at least partially below the swirl vanes. The bottom of the shield 14 preferably extends axially below the bottom of the contracting portion 12; e.g., below point P as shown in FIG. 1, or at least below the top of the contracting portion, e.g., below line 13, or below the bottom of the central hub if the central hub does not decrease in diameter at a lower section. Preferably, the bottom of the shield 14 is disposed axially below the bottom of the central hub 4.

The shield 14 can be made from essentially any suitable material. In an example embodiment, the shield is made from the same material as the swirl vanes 8, e.g., metals such as aluminum or steel. However, other materials are possible, and such materials can vary depending on the particular application. In an example embodiment for mounting the shield 14 within the cyclone 100, a surface at an upper diameter of the (generally cylindrical) shield is fixedly coupled, e.g., attached, and in a particular example welded, to a lower surface at one or more bottom portions (preferably, a plurality of bottom portions) of the swirl vanes 8, e.g., in the position shown in FIG. 1. Other example methods for mounting the shield 14 within the cyclone 100 include, but are not limited to, attaching (e.g., fastening) the shield to a plurality of attachment members (e.g., rods or other suitable members) (not shown) welded to the bottom of the swirl vanes 8, forming the swirl vanes and the shield as a unitary piece, etc.

In an example operation of the cyclone 100, passing an incoming gas stream 16 through the swirl vanes 8 induces a swirling flow in the annular section 6. The inner and outer annular portions 15a, 15b defined by the shield 14 divide this swirling flow respectively into inner and outer concentric swirling flows 17a, 17b. Particularly, the inner swirling flow 17a occurs within the inner annular portion 15a (radially between the outer diameter of the central hub 4 and the shield 14), and the outer swirling flow 17b occurs within the outer annular portion 15b (radially between the shield 14 and the inner diameter (wall) of the barrel 2).

In conventional cyclones, where the diameter of the central hub begins to decrease, the swirling flow of the incoming gas stream in the annular section contracts, or squeezes, to the center of the cyclone, with an associated increase in velocity and a low pressure region at the center. This in turn causes the gas at the inner diameter of the barrel to momentarily contract to a smaller diameter, causing an abrupt change, or acceleration, in the particle flow direction. This acceleration erodes the inner diameter of the barrel.

In the cyclone 100, a portion of the swirling flow from the gas stream 16 that exits the bottom of the swirl vanes 8 circumferentially between adjacent swirl vanes and radially between the central hub 4 and the shield 14 is directed into the inner annular portion 15a, providing the inner swirling flow 17a. Another portion of the swirling flow from the gas stream that exits the bottom of the swirl vanes 8 circumferentially between adjacent swirl vanes and radially between the shield 14 and the inner wall of the barrel 2 is directed into the outer annular portion 15b, providing the outer swirling flow 17b. The shield 14 protects the inner diameter of the barrel 2 from erosion due to the inner swirling flow 17a even when a vacuum is created in the center of the cyclone 100. The inner and outer swirling flows 17a, 17b can recombine below the shield 14.

A solid particle outlet 30 at a periphery of the barrel 2 is designed for removal of concentrated solids, in an underflow gas, which are forced to this radial periphery by centrifugal forces established in downwardly-flowing, swirling gas. The solid particle outlet 30 may be embodied in one or more openings (e.g., slots or holes) in the side of the barrel 2 or at its lower end. A purified gas outlet 52, concentric with the barrel 2, is designed for removal of a clean gas having a greatly reduced solids concentration, relative to the underflow gas.

Figure 2:
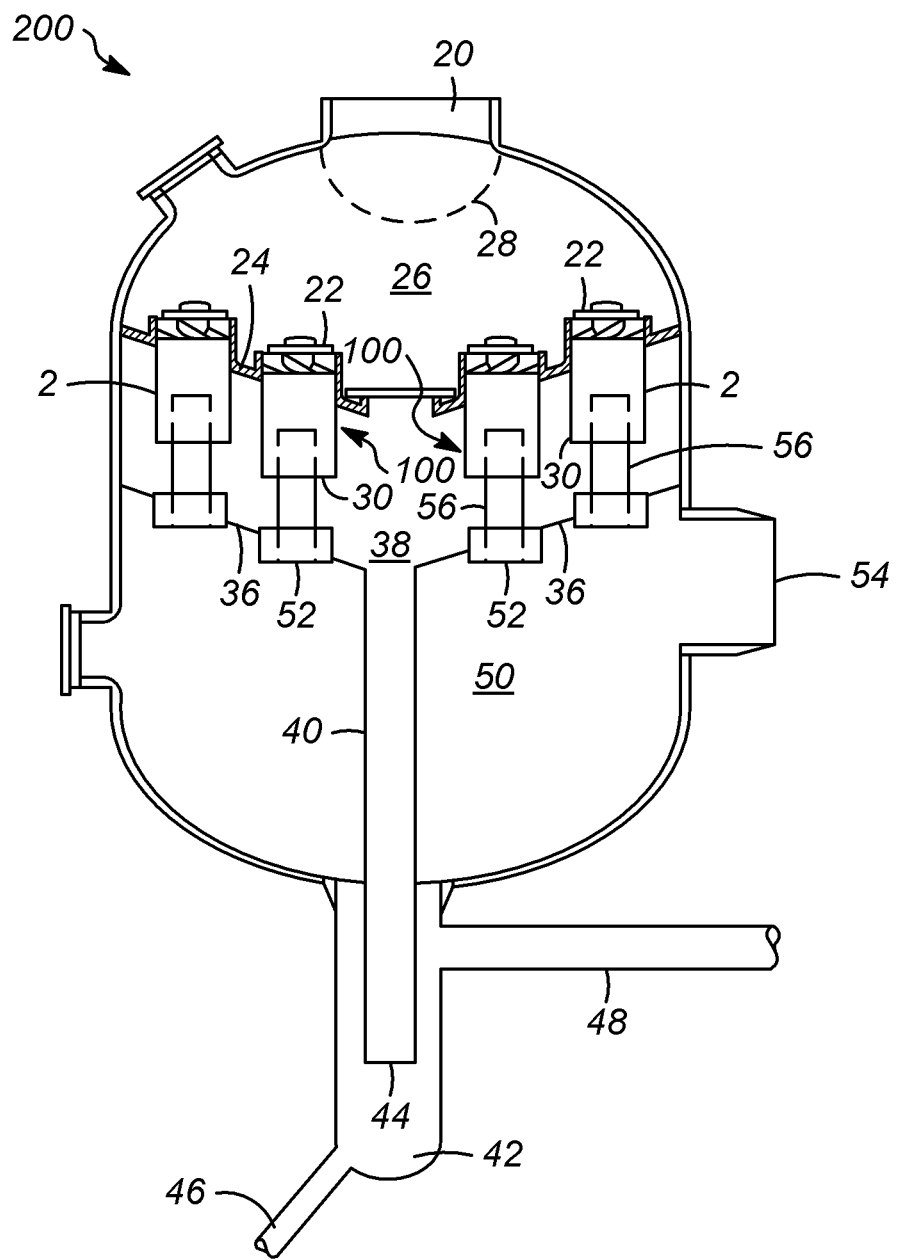
FIG. 2 is a side cut-out view taken along the axis of a solid-gas separator having a plurality of cyclones as shown in FIG. 1.

FIG. 2 depicts a gas-solid separator 200 such as a TSS, having a plurality of cyclones 100 as described herein. While only four cyclones 100 are represented in FIG. 2, between about 5 and 300 cyclones, and in some example embodiments between about 10 and about 200 cyclones, may be used depending on the particular gas-solid separation operation.

In operation, a gas stream is fed to the gas-solids separator 200 through a process gas inlet 20, which communicates with impure gas inlets 22 at upper ends of the barrels 2 of the plurality of cyclones 100, providing the gas stream 16 (FIG. 1) for each of the cyclones. The impure gas inlets 22 extend above an upper tube sheet 24. The upper tube sheet 24 at least partially defines an inlet chamber 26 that limits communication between this chamber and the rest of the gas-solid separator 200. The gas stream entering the gas-solid separator 200 may be distributed via a diffuser 28 to process gas inlets 22 of the plurality of cyclones 100 containing swirl vanes (eight in FIG. 1).

These swirl vanes restrict the gas stream flow path, thereby accelerating the flowing gas stream. The swirl vanes also impart a helical or spiral motion to the flowing gas stream. The shield 14 directs the swirling flow from the flowing gas stream into the inner annular portion 15a and the outer annular portion 15b, providing the inner and outer swirling flows 17a, 17b. Below the shield 14, the inner and outer swirling flows 17a, 17b force the higher-density solids toward the wall of the barrels 2 of the cyclones 100. Solid particles directed to the swirl periphery in this manner fall through the solid particle outlets 30 of the cyclones 100. Solid particle outlets 30, at lower ends of the barrels 2, extend to positions located between the upper tube sheet 24 and a lower tube sheet 36. A solids chamber 38 is therefore defined between these tube sheets 24, 36.

An underflow gas stream is withdrawn from a particle-rich gas outlet 44 in communication with the solid particle outlets 30 of the plurality of cyclones 100. The particle-rich gas outlet 44 is at a lower end of the solids outlet tube 40, extending from the solids chamber 38 into a collection vessel 42. The solids outlet tube therefore transports solids collected on the lower tube sheet 36 into this collection vessel 42. A high percentage of the solid particles contained in the total gas fed to the gas-solid separator 200, generally at least about 95% by weight, typically at least about 98% by weight, and often at least about 99% by weight, is transferred out of the collection vessel 42 via the solids outlet tube 40.

Underflow gas is therefore the portion, typically from about 1% to about 10% by volume, and often from about 3% to about 5% by volume, of the total gas fed to the gas-solid separator 200 that is directed to the solids outlet tube 40 and carries away the removed solid particles. The underflow may carry these solid particles into the collection vessel 42, where the level can be controlled by a slide valve (not shown) on a conduit 46. When a level of solids is established in the collection vessel 42, the underflow vapor can turn back up into the transfer pipe 48.

As shown in FIG. 2, the bottom of the gas-solid separator 200 may be defined by a hemispherical region that is a clean gas chamber 50. A clean gas flows down along the central axes (A-A' in FIG. 1) of the cyclones 100 and through purified gas outlets 52 extending below the lower tube sheet 36. A clean gas stream is therefore withdrawn from a particle-lean gas outlet 54 in communication with the purified gas outlets 52 of the plurality of cyclones 100. As shown in the example embodiment illustrated in FIG. 2, clean gas first passes through the open-ended cyclone gas outlet tubes 52 to below the lower tube sheet 36 and then into the clean gas chamber 50. The lower tube sheet 36 limits communication between the clean gas chamber 50 and the solids chamber 38. The clean gas stream that is withdrawn through the particle-lean gas outlet 54 represents the bulk of the gas stream fed to the gas-solid separator 200. The solids concentration of the clean gas is typically less than about 100 mg/Nm$^3$ and often less than about 50 mg/Nm$^3$. A representative gas-solid separator is generally capable of removing essentially all solid (e.g., catalyst) particles having a diameter of 20 microns or greater.

Example apparatuses and methods are provided for removing solid particles from gas streams, including refining and petrochemical process streams such as gas effluents from fluidized bed processes. Representative process streams include effluents from catalytic reaction zones and/or catalyst regeneration zones of FCC or MTO processes.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It will be understood that various changes may be made in the function and arrangement of elements described in an exemplary embodiment without departing from the scope of the invention as set forth in the appended claims.

What is claimed is:

1. A cyclone for a gas-solid separator, the cyclone comprising:
    a barrel;
    a central hub disposed within the barrel to provide an annular section between the central hub and the barrel, the central hub having a contracting portion;
    swirl vanes extending radially into the annular section; and
    a shield disposed at least partially within the annular section and at least partially below the swirl vanes, the shield radially dividing the annular section into an inner annular portion and an outer annular portion, a top of the shield is axially disposed above the contracting portion of the central hub.

2. The cyclone of claim 1, wherein the inner annular portion is defined radially between an outer diameter of the central hub and the shield, and wherein the outer annular portion is defined radially between the shield and an inner diameter of the barrel.

3. The cyclone of claim 1, wherein the inner annular portion defines a radial distance between about 10% and about 90% of an annulus of the annular section, and wherein the outer annular portion defines a remainder of the annulus of the annular section.

4. The cyclone of claim 1, wherein a bottom of the shield is axially disposed below the contracting portion of the central hub.

5. The cyclone of claim 1, wherein a top of the shield is axially disposed above a bottom of the central hub.

6. The cyclone of claim 1, wherein a bottom of the shield is axially disposed below the bottom of the central hub.

7. The cyclone of claim 1, wherein the shield is fixedly coupled to one or more bottom portions of the swirl vanes.

8. A gas-solid separator comprising an upper tube sheet, a lower tube sheet, and at least one cyclone extending through the tube sheets, the cyclone comprising an impure gas inlet at an upper end of a barrel above the upper tube sheet, a solid particle outlet at a lower end of the barrel between the upper tube sheet and the lower tube sheet, and a purified gas outlet below the lower tube sheet, wherein the cyclone further comprises:
    a barrel;
    a central hub disposed within the barrel to provide an annular section between the central hub and the barrel;
    swirl vanes extending radially into the annular section; and
    a shield disposed at least partially within the annular section and at least partially below the swirl vanes, the shield radially dividing the annular section into an inner annular portion and an outer annular portion and a top of the shield is axially disposed above a bottom of the central hub.

9. The gas-solid separator of claim 8, comprising a plurality of cyclones, each comprising an impure gas inlet at an upper end of a barrel above the upper tube sheet, a solid particle outlet at a lower end of the barrel between the upper tube sheet and the lower tube sheet, and a purified gas outlet below the lower tube sheet, each cyclone further comprising:
    a barrel;
    a central hub disposed within the barrel to provide an annular section disposed between the central hub and the barrel;
    swirl vanes extending radially into the annular section; and
    a shield disposed at least partially within the annular section and at least partially below the swirl vanes, the shield radially dividing the annular section into an inner annular portion and an outer annular portion.

10. The gas-solid separator of claim 9, wherein the plurality of cyclones number from about 5 to about 300 cyclones.

11. The gas-solid separator of claim 10, further comprising a process gas inlet in communication with the impure gas inlets of the plurality of cyclones.

12. The gas-solid separator of claim 11, further comprising a particle-rich gas outlet in communication with the solid particle outlets of the plurality of cyclones.

13. The gas-solid separator of claim 12, further comprising a particle-lean gas outlet in communication with the purified gas outlets of the plurality of cyclones.

14. A cyclone for a gas-solid separator, the cyclone comprising:
    a barrel;

a central hub disposed within the barrel to provide an annular section between the central hub and the barrel;

swirl vanes extending radially into the annular section; and a shield disposed at least partially within the annular section and at least partially below the swirl vanes, the shield radially dividing the annular section into an inner annular portion and an outer annular portion, the shield being fixedly coupled to one or more bottom portions of the swirl vanes.

15. The cyclone of claim 14, wherein the inner annular portion is defined radially between an outer diameter of the central hub and the shield, and wherein the outer annular portion is defined radially between the shield and an inner diameter of the barrel.

16. The cyclone of claim 14, wherein the inner annular portion defines a radial distance between about 10% and about 90% of an annulus of the annular section, and wherein the outer annular portion defines a remainder of the annulus of the annular section.

17. The cyclone of claim 14, wherein a top of the shield is axially disposed above a contracting portion of the central hub.

18. The cyclone of claim 17, wherein a bottom of the shield is axially disposed below the contracting portion of the central hub.

19. The cyclone of claim 14, wherein a top of the shield is axially disposed above a bottom of the central hub.

20. The cyclone of claim 14, wherein a bottom of the shield is axially disposed below the bottom of the central hub.

* * * * *